(12) United States Patent
Kim et al.

(10) Patent No.: US 8,409,586 B2
(45) Date of Patent: Apr. 2, 2013

(54) STABLE LIQUID FORMULATION OF HUMAN GROWTH HORMONE

(75) Inventors: Sun hee Kim, Cheongju-si (KR); Yo kyung Chung, Yongin-si (KR); Jae young Chang, Daejeon (KR); Sang kil Lee, Yongin-si (KR); Min suk Lee, Seoul (KR); Seung kook Park, Seongnam-si (KR)

(73) Assignee: Daewoong Co., Ltd. (KR)

( * ) Notice: Subject to any disclaimer, the term of this patent is extended or adjusted under 35 U.S.C. 154(b) by 357 days.

(21) Appl. No.: 12/307,661

(22) PCT Filed: Jul. 6, 2006

(86) PCT No.: PCT/KR2006/002640
§ 371 (c)(1),
(2), (4) Date: Aug. 18, 2009

(87) PCT Pub. No.: WO2008/004717
PCT Pub. Date: Jan. 10, 2008

(65) Prior Publication Data
US 2009/0298768 A1    Dec. 3, 2009

(51) Int. Cl.
*A61K 38/27* (2006.01)
*A61K 38/17* (2006.01)
*A61K 38/18* (2006.01)
*A61K 47/42* (2006.01)

(52) U.S. Cl. .................. 424/198.1; 424/497; 530/351

(58) Field of Classification Search .......... None
See application file for complete search history.

(56) References Cited

U.S. PATENT DOCUMENTS 6,448,225 B2    9/2002  O'Connor et al.

FOREIGN PATENT DOCUMENTS

| EP | 0 303 746 A1 | 2/1989 |
|---|---|---|
| EP | 0 303 746 B1 | 11/1992 |
| JP | 7-509719 A | 10/1995 |
| KR | 10-1987-0000701 | 4/1987 |
| KR | 19947003688 A | 12/1994 |
| KR | 1019970006498 A | 2/1997 |
| KR | 10-1999-0072277 | 9/1999 |
| KR | 10-2000-0019788 | 4/2000 |
| KR | 10-2000-0037747 | 7/2000 |
| KR | 10-2005-0023875 | 3/2005 |
| WO | 94/03198 A1 | 2/1994 |
| WO | 97/39768 | 10/1997 |
| WO | 01/24814 | 4/2001 |
| WO | 01/26692 | 4/2001 |
| WO | WO/01/24814 * | 4/2001 |
| WO | 02/00261 | 1/2002 |
| WO | 2005/027960 | 3/2005 |
| WO | 2005/028516 A2 | 3/2005 |
| WO | 2005/051448 A1 | 6/2005 |
| WO | 2005/063298 A1 | 7/2005 |
| WO | WO/2005/063298 * | 7/2005 |

OTHER PUBLICATIONS

International Search Report—PCT/KR2006/002640 dated Feb. 14, 2007.
Written Opinion—PCT/KR2006/002640 dated Feb. 14, 2007.
Chinese Office Action for Application No. 200680055699.5 dated Feb. 23, 2011.

* cited by examiner

*Primary Examiner* — Elly-Gerald Stoica
(74) *Attorney, Agent, or Firm* — Cantor Colburn LLP

(57) ABSTRACT

Disclosed herein is a stable liquid formulation comprising human growth hormone; L-lysine, L-arginine or polyethylene glycol 300; and poly(oxyethylene) poly(oxypropylene) copolymer, polyethylene glycol-15 polyoxystearate or polyethylene glycol-35 castor oil.

4 Claims, 2 Drawing Sheets

STABLE LIQUID FORMULATION OF HUMAN GROWTH HORMONE

TECHNICAL FIELD

The present invention relates to a stable liquid formulation comprising human growth hormone; L-lysine, L-arginine or polyethylene glycol 300; and poly(oxyethylene) poly(oxypropylene) copolymer, polyethylene glycol-15 poly-oxystearate or polyethylene glycol-35 castor oil.

BACKGROUND ART

Human growth hormone, which is produced in the human pituitary gland, is a single-chain polypeptide of 191 amino acids having a molecular weight of about 22,000 daltons. Human growth hormone is used mainly for treating pituitary dwarfism in children (Endocrinol. Rev. 4, 155, 1983).

Human growth hormone tends to be unstable in pharmaceutical preparations. The degradation products of growth hormone, including deamidated or sulfoxylated products and dimer or polymer forms, can be generated in solution. A predominant chemical degradation reaction of human growth hormone is deamidation, which especially takes place at the asparagine residue at position 149, by direct hydrolysis or via a cyclic succinimide intermediate to form L-asp-hGH, L-iso-asp-hGH, D-asp-hGH and D-iso-asp-hGH. At present, these deamidated products of human growth hormone are not believed to have toxic or altered biological activity or receptor binding properties, but the conformational stability of the sulfoxides is reduced compared to native human growth hormone.

The deamidated human growth hormone is undesirable for use as a medicament because it undergoes quality deterioration, despite having unaltered biological activity, and its allowable content is thus usually provided by the public specification for purity. Also, the formation of aggregates of growth hormone, such as dimers or polymers, causes undesired immunogenicity, leading to a safety problem in vivo, and suspended solids, leading to an appearance problem, thereby causing patients displeasure.

Protein stability is closely related with water. Human growth hormone is mostly commercially available in a lyophilized formulation to increase its stability that must be reconstituted prior to use. However, many studies have been conducted on liquid formulations of human growth hormone in order to improve the convenience of medical doctors and patients. For example, U.S. Pat. No. 6,448,225, relating to Genentech's Nutropin AQ, discloses an aqueous formulation of human growth hormone, comprising human growth hormone, mannitol, a buffer and a non-ionic surfactant, wherein citrate buffer was exemplified as being preferable. Korean Pat. Application No. 10-1999-0001217 provides a stable aqueous formulation, in which human growth hormone is dissolved in a buffer solution, which is prepared using a slightly to moderately acidic buffer, preferably a maleate buffer, containing benzalkonium chloride. Korean Pat. Application No. 10-1998-0052483 describes a pharmaceutically-stable liquid formulation of human growth hormone, wherein a buffer solution consisting of sodium acetate and sodium glutamate is preferred. Also, in Korean Pat. Application No. 10-1994-0702139, Novo Nordisk A/S describes a pharmaceutical formulation comprising a growth hormone, and an amino acid selected from the group consisting of Asp, Ile, Val, Leu and His, or a derivative of histidine, or a peptide comprising at least one basic amino acid and at least one acidic amino acid, and a non-ionic detergent, such as polysorbate or poloxamer. Novo Nordisk A/S currently markets Norditropin SimpleXx, which contains human growth hormone, histidine buffer, a non-ionic surfactant, sodium chloride, and a preservative.

However, although a variety of attempts have been made to provide an liquid formulation of growth hormone, as described above, there is a need for a stabler liquid formulation of growth hormone.

DISCLOSURE OF INVENTION

Technical Problem

It is therefore an object of the present invention to provide a stable liquid formulation of human growth hormone by combining a specific amino acid, such as L-lysine or L-arginine, or polyethylene glycol, with a specific surfactant in order to minimize the formation of deamidated products and aggregation, thereby enhancing long-term storage stability and convenience relative to known liquid formulations.

BEST MODE FOR CARRYING OUT THE INVENTION

Figure 1:
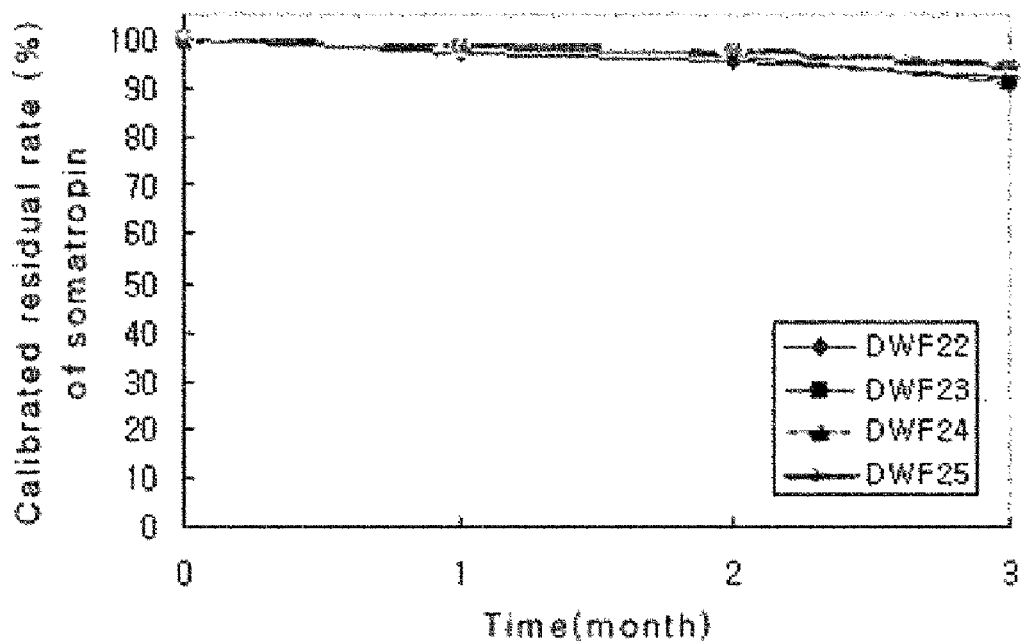
FIG. 1 is a graph showing the residual rate (%) of human growth hormone according to deamidation and aggregation when a liquid formulation according to the present invention is stored at 25° C. for three months.
Figure 1:
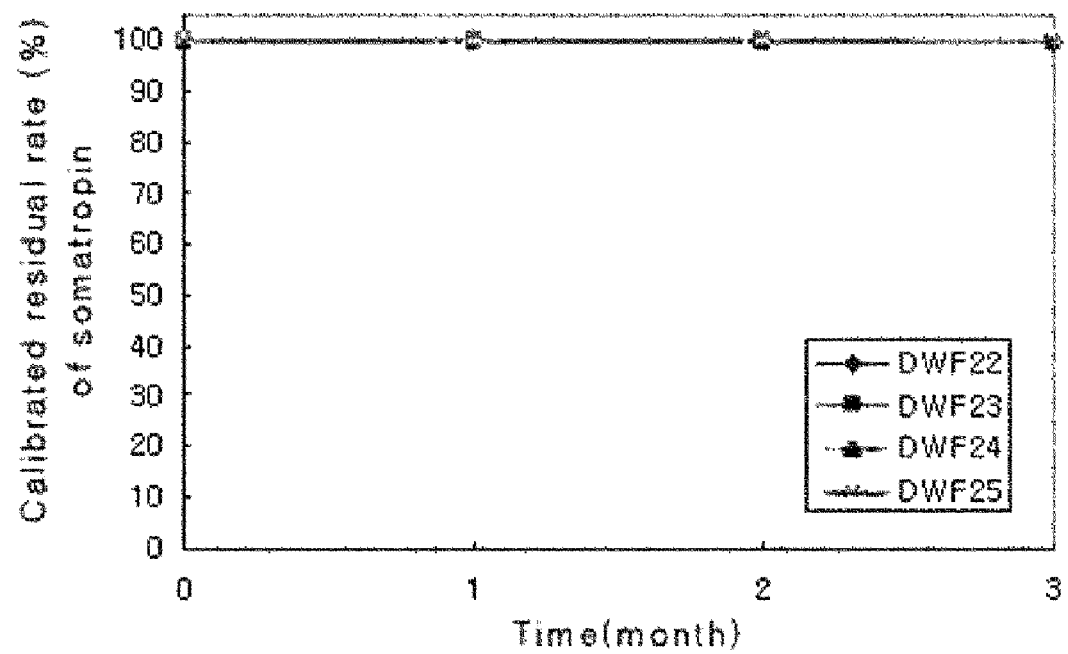

In one aspect, the present invention relates to a stable liquid formulation comprising human growth hormone; L-lysine or L-arginine; and poly(oxyethylene) poly(oxypropylene) copolymer, polyethylene glycol-15 polyoxystearate or polyethylene glycol-35 castor oil.

Human growth hormone, which is intended to be stabilized in the liquid formulation of the present invention, may be naturally occurring, or may be obtained from a prokaryote or eukaryote transformed with DNA coding for human growth hormone using a recombinant DNA technique. A method of producing human growth hormone using E. coli or yeast as a gene recombinant host is described in the literature, for example, Korean Pat. No. 25013, Korean Pat. No. 316347, or Korean Pat. Publication No. 10-1997-0006498. The human growth hormone may be the wild type or a derivative thereof.

The liquid formulation of the present invention comprises L-lysine or L-arginine as a stabilizer. Preferred is a salt form of the stabilizer, for example, L-lysine hydrochloride or L-arginine hydrochloride. The stabilizers exhibited a good effect of causing no aggregation after storage for a predetermined period of time in the liquid formulation of human growth hormone compared to other conventional amino acid stabilizers. The aforementioned stabilizers, as shown in Table 8, underwent no aggregation after 14 days, and thus displayed good stability compared to histidine, which is employed in International Pat. Publication No. WO 1997/39768. In the provision of a stable liquid formulation of human growth hormone, these results exhibit a good effect that was not disclosed in the aforementioned cited patent, disclosing only the use of an amino acid as a stabilizer, and other known literature.

The poly(oxyethylene) poly(oxypropylene) copolymer (poloxamer), macrogol-15 polyoxystearate (polyethylene glycol-15 polyoxystearate) or cremophor ELP (polyethylene glycol-35 castor oil), used in the liquid formulation of the present invention, is a non-ionic surfactant. When the present inventors employed the aforementioned surfactants, among various non-ionic surfactants, to combine them with a specific stabilizer, the liquid formulation was found to have enhanced stability. These surfactants displayed good effects with respect to the deamidation and aggregation of human growth hormone compared to conventional polysorbates, such as Tween 20 or Tween 80 (Table 5). The poloxamer is preferably poloxamer 188 (poly(oxyethylene) poly(oxypropylene) copolymer 188) or poloxamer 407 (poly(oxyethylene) poly(oxypropylene) copolymer 407), and more preferably poloxamer 188 (poly(oxyethylene) poly(oxypropylene) copolymer 188).

The liquid formulation of the present invention may further include an additive known in the art, for example, a buffer, an isotonic agent, a preservative or an analgesic.

The buffer may be used to adjust the pH value of the liquid formulation with no effect on human growth hormone, and is exemplified by acetate, glutamate, lactate, malate, citrate and phosphate. Sodium citrate or sodium acetate is preferred. As is apparent from the results of Example 4, the buffer does not affect the stability of the liquid formulation of the present invention. These results are obtained because the good stability of the liquid formulation of the present invention results from the combination of a specific stabilizer and a specific surfactant. The buffer is present at a concentration of 5 to 100 mM, and preferably 5 to 50 mM, in the liquid formulation of the present invention.

The isotonic agent useful in the present invention may include sodium chloride, mannitol, sucrose, dextrose, sorbitol, or mixtures thereof. D-mannitol is preferred. The isotonic agent is preferably present at a concentration of 20 to 50 mg/ml in the liquid formulation of the present invention.

The preservative useful in the present invention may include benzyl alcohol, phenol, and meta-cresol. Benzyl alcohol is preferred. The benzyl alcohol serves as an analgesic as well as a preservative. The preservative is preferably present in an amount ranging from 1 to 9 mg/ml in the present liquid formulation.

In a detailed aspect, the liquid formulation of the present invention comprises 2.5 to 7.5 mg/ml of human growth hormone 0.01 to 1.0% (w/v) of L-lysine or L-arginine per D of human growth hormone and 0.01 to 1.0% (w/v) of poly(oxyethylene) poly(oxypropylene) copolymer, polyethylene glycol-15 polyoxystearate or polyethylene glycol-35 castor oil. In a further detailed aspect, the liquid formulation comprises 2.5 to 5.5 mg/ml of human growth hormone; 0.02 to 0.5% (w/v) of L-lysine or L-arginine per mg of human growth hormone; and 0.1 to 0.5% (w/v) of poly (oxy ethylene) poly(oxypropylene) copolymer, polyethylene glycol-15 polyoxystearate or polyethylene glycol-35 castor oil.

In a preferred aspect, the liquid formulation of human growth hormone according to the present invention comprises 2.5 to 5.5 mg/ml of human growth hormone; 0.02 to 0.5% (w/v) of L-lysine or L-arginine per D of human growth hormone; 0.1 to 0.5% (w/v) of poly(oxyethylene) poly(oxypropylene) copolymer, polyethylene glycol-15 polyoxystearate or polyethylene glycol-35 castor oil 5 to 20 mM of sodium citrate or sodium acetate; 20 to 50 mg/ml of D-mannitol; and 1 to 9 mg/ml of benzyl alcohol. The liquid formulation is moderately acidic or neutral, and preferably has a pH value between 5.8 and 7.0, and more preferably a pH value between 6.0 and 6.2.

In another aspect, the present invention relates to a stable liquid formulation comprising human growth hormone; polyethylene glycol 300; and poly(oxyethylene) poly(oxypropylene) copolymer, polyethylene glycol-15 polyoxystearate or polyethylene glycol-35 castor oil.

The human growth hormone and the poly(oxyethylene) poly(oxypropylene) copolymer, polyethylene glycol-15 polyoxystearate or polyethylene glycol-35 castor oil contained in the liquid formulation are the same as described above.

The liquid formulation of the present invention may include polyethylene glycol 300 as a stabilizer. Polyethylene glycol is a useful polymer that is water-soluble and dissolved in various organic solvents. Since polyethylene glycol is non-toxic and rapidly cleared from the body, it is used for a stable pharmaceutical composition (International Pat. Publication No. WO 01/26692). Korean Pat. Application No. 10-2003-0061434 discloses a liquid formulation of human growth hormone, comprising polyethylene glycol instead of polysorbate as a non-ionic surfactant, and not containing an antiseptic such as benzyl alcohol or phenol. However, this application describes the use of 0.001 to 20 mg/ml of polyethylene glycol having a molecular weight higher than 3,000 Da among polyethylene glycols, without using a surfactant. This is in contrast to the present invention, which employs polyethylene glycol having a molecular weight of 300 Da, i.e., polyethylene glycol 300, along with a specific surfactant in order to improve the stability of the liquid formulation. The present invention reduces aggregation through the combinational use of a specific polyethylene glycol and a specific surfactant, as described above, thereby enabling the long-term storage of a liquid formulation.

The above liquid formulation of the present invention may further include an additive known in the art, for example, a buffer, an isotonic agent, a preservative or an analgesic. The buffer, isotonic agent, preservative or analgesic is the same as described above.

In a detailed aspect, the liquid formulation of the present invention comprises 2.5 to 7.5 mg/ml of human growth hormone; 0.1 to 5.0% (v/v) of polyethylene glycol 300 per mg of human growth hormone; and 0.01 to 1.0% (w/v) of poly (oxyethylene) poly(oxypropylene) copolymer, polyethylene glycol-15 polyoxystearate or polyethylene glycol-35 castor oil. In a further detailed aspect, the liquid formulation comprises 2.5 to 5.5 mg/ml of human growth hormone; 0.2 to 1.0% (v/v) of polyethylene glycol 300 per mg of human growth hormone; and 0.1 to 0.5% (w/v) of poly(oxyethylene) poly(oxypropylene) copolymer, polyethylene glycol-15 polyoxystearate or polyethylene glycol-35 castor oil.

In a preferred aspect, the liquid formulation of human growth hormone according to the present invention comprises 2.5 to 5.5 mg/ml of human growth hormone; 0.2 to 1.0% (v/v) of polyethylene glycol 300 per mg of human growth hormone; 0.1 to 0.5% (w/v) of poly(oxyethylene) poly(oxypropylene) copolymer, polyethylene glycol-15 polyoxystearate or polyethylene glycol-35 castor oil 5 to 20 mM of sodium citrate or sodium acetate; 20 to 50 mg/ml of D-mannitol; and 1 to 9 mg/ml of benzyl alcohol. The liquid formulation is moderately acidic or neutral, preferably has a pH value between 5.8 and 7.0, and more preferably has a pH value between 6.0 and 6.2.

MODE FOR THE INVENTION

A better understanding of the present invention may be obtained through the following examples which are set forth to illustrate, but are not to be construed as the limit of the present invention.

EXAMPLE 1

Preparation and Analysis of a Liquid Formulation of Human Growth Hormone

A liquid formulation according to the present invention was prepared as follows. 4.0 mg/ml of native human growth hormone (Daewoong, Korea), which was provided in a bulk solution prior to being lyophilized, were mixed with a 10 mM aqueous solution of sodium acetate (Sigma), sodium citrate (Sigma) or sodium phosphate monobasic (Sigma) as a buffer so as to be adjusted to a pH ranging from 6.0 to 6.2. After the solution was adjusted to the final concentration, it was mixed with an excipient (D-mannitol, Sigma), a surfactant {macrogol-15 polyoxystearate (Solutol HS 15, BASF), poloxamer 188 (Lutrol F 68, BASF), poloxamer 407 (Lutrol F 127, BASF), cremophor ELP (BASF), Tween 20 (CRILLET 1 HP, Croda) or Tween 80 (CRILLET 4 HP, Croda)}, a stabilizer (polyethylene glycol 300 (PEG 300, BASF), polyethylene glycol 400 (PEG 400, BASF), PVPK-12 (Kollidon 12 PF, BASF), PVPK-15 (Kollidon 15 PF, BASF), L-lysine (L-Lysine-HCl, Sigma) or L-arginine (L-Arginine-HCl, Sigma)), and benzyl alcohol (Daejung, Korea) as a preservative.

The resulting liquid formulation was stored under strict conditions of 40° C. and 75% RH for two weeks. The formulation was examined for the stability of human growth hormone according to deamidation and polymerization over time. Deamidation was determined using reverse-phase HPLC (RP-HPLC), and the formation of dimers and polymers by size exclusion HPLC (SEC-HPLC), according to the European Pharmacopoeia method (EP method).

EXAMPLE 2

Evaluation of Effects of Surfactants on the Stability of Human Growth Hormone

In order to investigate the effects of pharmaceutically acceptable surfactants on the stability of human growth hormone, liquid formulations of human growth hormone were prepared using the components listed in Table 1 and then analyzed according to the same method as in Example 1.

TABLE 1

|  | Major Component | Buffer | Isotonic Agent | Surfactant | Preservative | Solution |
|---|---|---|---|---|---|---|
| Control | Somatropin 3.3 mg | Sodium acetate 10 mM | D-mannitol 50 mg | — | Benzyl alcohol 2.5 mg | Injectable solution 1 ml |
| DWF 1 | Somatropin 3.3 mg | Sodium acetate 10 mM | D-mannitol 50 mg | Tween 20 2 mg | Benzyl alcohol 2.5 mg | Injectable solution 1 ml |
| DWF 2 | Somatropin 3.3 mg | Sodium acetate 10 mM | D-mannitol 50 mg | Macrogol-15 poly-oxystearate 2 mg | Benzyl alcohol 2.5 mg | Injectable solution 1 ml |
| DWF 3 | Somatropin 3.3 mg | Sodium acetate 10 mM | D-mannitol 50 mg | Cremophor ELP 2 mg | Benzyl alcohol 2.5 mg | Injectable solution 1 ml |
| DWF 4 | Somatropin 3.3 mg | Sodium acetate 10 mM | D-mannitol 50 mg | Tween 80 2 mg | Benzyl alcohol 2.5 mg | Injectable solution 1 ml |
| DWF 5 | Somatropin 3.3 mg | Sodium acetate 10 mM | D-mannitol 50 mg | Poloxamer 188 2 mg | Benzyl alcohol 2.5 mg | Injectable solution 1 ml |

The liquid formulations thus prepared were evaluated for the deamidation and aggregation of human growth hormone according to the type of surfactants, and the results are given in Table 2, below.

In Table 2, deamidation (%) indicates the calibrated residual rate (%) of non-deamidated active human growth hormone, and aggregation indicates the calibrated residual rate (%) of active human growth hormone not forming dimers or polymers, according to time at 40° C.

TABLE 2

|  |  | Control (—) | DWF 1 (Tween20) | DWF2 (Macrogol-15 poly-oxystearate) | DWF3 (cremophor ELP) | DWF4 (Tween 80) | DWF5 (poloxamer 188) |
|---|---|---|---|---|---|---|---|
| Deamidation (SomatropIn %) | Day 8 | 65.2 ± 0.5 | 81.9 ± 0.3 | 83.1 ± 0.3 | 83.4 ± 0.2 | 82.7 ± 0.2 | 83.1 ± 0.3 |
|  | Day 14 | 45.5 ± 0.4 | 69.1 ± 0.2 | 68.5 ± 0.4 | 69.1 ± 0.2 | 68.9 ± 0.2 | 69.6 ± 0.2 |
| Aggregation (Somatropin %) | Day 8 | 98.0 ± 0.2 | 100.0 ± 0.0 | 100.0 ± 0.0 | 100.0 ± 0.0 | 99.9 ± 0.1 | 100.0 ± 0.0 |
|  | Day 14 | 80.2 ± 0.3 | 99.4 ± 0.1 | 99.1 ± 0.1 | 99.6 ± 0.1 | 99.7 ± 0.1 | 99.5 ± 0.1 |

Compared to the control, formulations preparing using surfactants were found to suppress deamidation and aggregation. These results indicate that the use of a surfactant improves the stability of a liquid formulation of human growth hormone.

EXAMPLE 3

Evaluation of Effects of Stabilizers on the Stability of Human Growth Hormone

In order to investigate the stability of a liquid formulation of human growth hormone according to stabilizers, liquid formulations of human growth hormone were prepared using the components listed in Table 3 and then analyzed according to the same method as in Example 1.

TABLE 3

|  | Major component | Buffer | Isotonic agent | Surfactant | Stabilizer | Preservative | Solution |
| --- | --- | --- | --- | --- | --- | --- | --- |
| Control | Somatropin 3.3 mg | Sodium acetate 10 mM | D-mannito 150 mg | Tween 202 mg | — | Benzyl alcohol 2.5 mg | Injectable Solution 1 ml |
| DWF 6 | Somatropin 3.3 mg | Sodium acetate 10 mM | D-mannito 150 mg | Tween 202 mg | PEG 300 1% v/v | Benzyl alcohol 2.5 mg | Injectable Solution 1 ml |
| DWF 7 | Somatropin 3.3 mg | Sodium acetate 10 mM | D-mannito 150 mg | Tween 202 mg | PEG 400 1% v/v | Benzyl alcohol 2.5 mg | Injectable Solution 1 ml |
| DWF 8 | Somatropin 3.3 mg | Sodium acetate 10 mM | D-mannito 150 mg | Tween 202 mg | PVP K-12 5 mg | Benzyl alcohol 2.5 mg | Injectable Solution 1 ml |
| DWF 9 | Somatropin 3.3 mg | Sodium acetate 10 mM | D-mannito 150 mg | Tween 202 mg | PVP K-17 5 mg | Benzyl alcohol 2.5 mg | Injectable Solution 1 ml |
| DWF 10 | Somatropin 3.3 mg | Sodium acetate 10 mM | D-mannito 150 mg | Tween 202 mg | L-Lys•HCl 1 mg | Benzyl alcohol 2.5 mg | Injectable Solution 1 ml |
| DWF 11 | Somatropin 3.3 mg | Sodium acetate 10 mM | D-mannito 150 mg | Tween 202 mg | L-Lys•HCl 1 mg | Benzyl alcohol 2.5 mg | Injectable Solution 1 ml |

The liquid formulations thus prepared were estimated for deamidation and aggregation according to the type of stabilizers, and the results are given in Table 4, below.

TABLE 4

|  | Deamidation (somatropin %) | | Aggregation (somatropin %) | |
| --- | --- | --- | --- | --- |
|  | Day 7 | Day 14 | Day 7 | Day 14 |
| Control (-) | 70.8 ± 0.2 | 52.0 ± 0.3 | 100.0 ± 0.0 | 97.0 ± 0.2 |
| DWF6 (PEG 300) | 83.7 ± 0.1 | 70.6 ± 0.2 | 100.0 ± 0.0 | 99.6 ± 0.1 |
| DWF7 (PEG 400) | 79.7 ± 0.1 | 66.9 ± 0.1 | 100.0 ± 0.0 | 99.3 ± 0.1 |
| DWF8 (PVP K-12) | 80.8 ± 0.2 | 69.0 ± 0.2 | 100.0 ± 0.0 | 99.5 ± 0.1 |
| DWF9 (PVP K-17) | 80.7 ± 0.2 | 69.0 ± 0.2 | 100.0 ± 0.0 | 99.4 ± 0.1 |
| DWF10 (L-Lys□HCl) | 83.3 ± 0.1 | 70.4 ± 0.1 | 100.0 ± 0.0 | 100.0 ± 0.0 |
| DWF11 (L-Agn□HCl) | 83.5 ± 0.1 | 70.2 ± 0.1 | 100.0 ± 0.0 | 100.0 ± 0.0 |

As shown in Table 4, among the stabilizers that were used, PEG 300 (polyethylene glycol 300) and two amino acids, L-Lys □ HCl and L-Arg □ HCl, were found to stabilize human growth hormone. In particular, when L-lysine and L-arginine were used, aggregation was suppressed to a relatively high degree in a formulation.

EXAMPLE 4

Evaluation of Effects of Buffers on the Stability of Human Growth Hormone

The liquid formulation containing PEG 300, which was proven to stabilize human growth hormone in a liquid formulation in Example 3, was further examined for the stability of human growth hormone according to the type of buffers.

Liquid formulations of human growth hormone were prepared from the components listed in Table 5 according to the same method as in Example 1.

TABLE 5

|  | Major component | Buffer | Isotonic agent | Surfactant | Stabilizer | Preservative | Solution |
|---|---|---|---|---|---|---|---|
| DWF12 | Somatropin 3.3 mg | Sodium acetate 10 mM | D-mannito 150 mg | Tween 202 mg | PEG 3001% v/v | Benzyl alcohol 2.5 mg | Injectable solution 1 ml |
| DWF13 | Somatropin 3.3 mg | Sodium citrate 10 mM | D-mannito 150 mg | Tween 202 mg | PEG 3001% v/v | Benzyl alcohol 2.5 mg | Injectable solution 1 ml |
| DWF14 | Somatropin 3.3 mg | Sodium phosphate 10 mM | D-mannito 150 mg | Tween 202 mg | PEG 3001% v/v | Benzyl alcohol 2.5 mg | Injectable solution 1 ml |

The stability of the liquid formulations thus prepared according to the type of buffers was determined by analyzing the formation of deamidated forms and dimers/polymers of human growth hormone over time at 40° C. The residual rates of active human growth hormone were described in Table 6, below.

TABLE 6

|  | Deamidation (somatropin %) | | Aggregation (somatropin %) | |
|---|---|---|---|---|
|  | Day 7 | Day 14 | Day 7 | Day 14 |
| DWF12 (sodium acetate) | 83.7 ± 0.1 | 70.6 ± 0.2 | 100.0 ± 0.0 | 99.27 ± 0.3 |
| DWF13 (sodium citrate) | 82.7 ± 0.5 | 70.9 ± 0.1 | 100.0 ± 0.0 | 99.62 ± 0.1 |
| DWF14 (sodium phosphate) | 80.8 ± 0.4 | 69.0 ± 0.3 | 100.0 ± 0.0 | 99.12 ± 0.4 |

The buffers were conventionally described as being important in a liquid formulation of human growth hormone in the aforementioned patent and applications (U.S. Pat. No. 6,448,225, Korean Pat. Application No. 10-1999-0001217, and Korean Pat. Application No. 10-1998-0052483). However, the liquid formulation of the present invention, as shown in Table 6, exhibited no marked difference in stability depending to the type of conventionally used buffer.

EXAMPLE 5

Comparison of Stability of Liquid Formulations

In order to compare the stability of liquid formulations according to the present invention, two control liquid formulations (control 1 and control 2) were prepared using the components listed in Table 7, below, and compared with human growth hormone (hGH) liquid formulations prepared according to the same method as in Example 1.

TABLE 7

|  | Major component | Buffer | Isotonic agent | Surfactant | Stabilizer | Preservative | Solution |
|---|---|---|---|---|---|---|---|
| Control 1 | Somatropin 2.7 mg | Sodium acetate | D-mannito 1 | Tween 20 | — | Benzyl alcohol | Injectable solution 1 ml |
| Contol 2 | Somatropin 3.3 mg | — | D-mannito 1 | Poloxamer 188 | Histidine | Phenol | Injectable solution 1 ml |
| DWF15 | Somatropin 2.5 mg | Sodium acetate 10 mM | D-mannito 135 mg | Macrogol-15 poly-oxystearate 2 mg | PEG 3001% v/v | Benzyl alcohol 2.5 mg | Injectable solution 1 ml |
| DWF16 | Somatropin 5.0 mg | Sodium acetate 10 mM | D-mannito 130 mg | Macrogol-15 poly-oxystearate 2 mg | PEG 4001% v/v | Benzyl alcohol 2.5 mg | Injectable solution 1 ml |
| DWF17 | Somatropin 2.5 mg | Sodium acetate 10 mM | D-mannito 138 mg | Poloxamer 188 2 mg | L-Lys•HCl 1 mg | Benzyl alcohol 2.5 mg | Injectable solution 1 ml |
| DWF18 | Somatropin 5.0 mg | Sodium acetate 10 mM | D-mannito 138 mg | Poloxamer 188 2 mg | L-Lys•HCl 2 mg | Benzyl alcohol 2.5 mg | Injectable solution 1 ml |
| DWF19 | Somatropin 2.5 mg | Sodium acetate 10 mM | D-mannito 138 mg | Poloxamer 188 2 mg | L-Lys•HCl 1 mg | Benzyl alcohol 2.5 mg | Injectable solution 1 ml |
| DWF20 | Somatropin 5.0 mg | Sodium acetate 10 mM | D-mannito 138 mg | Poloxamer 188 2 mg | L-Lys•HCl 2 mg | Benzyl alcohol 2.5 mg | Injectable solution 1 ml |

The hGH liquid formulations thus prepared were stored for 14 days under conditions of 40° C. and 75% RH. Then, the residual rates of somatropin were determined using SEC-HPLC. Also, the formulations were incubated at 2° C. to 8° C. for 24 hours with horizontal agitation (20 mm in amplitude, 220 oscillations per min), and were then examined for aggregation and appearance. The results are given in Table 8, below.

TABLE 8

| | 40° C., 75% RH | Agitation for 24 hrs | |
|---|---|---|---|
| | Aggregation Day 14 (somatropin %) | Aggregation Day 14 (somatropin %) | Appearance |
| Control 1 | 97.00 ± 0.15 | 94.57 ± 0.05 | ○○ |
| Control 2 | 99.11 ± 0.05 | 96.26 ± 0.07 | ○ |
| DWF15 | 99.99 ± 0.01 | 99.99 ± 0.01 | X |
| DWF16 | 98.22 ± 0.06 | 97.01 ± 0.15 | ○ |
| DWF17 | 100.00 ± 0.00 | 100.00 ± 0.00 | X |
| DWF18 | 99.98 ± 0.01 | 99.97 ± 0.02 | X |
| DWF19 | 100.00 ± 0.00 | 100.00 ± 0.00 | X |
| DWF20 | 100.00 ± 0.00 | 99.98 ± 0.01 | X |

Clear and transparent (X) Slightly produced (Δ) Turbid (○) Very High aggregate production (○○)

As shown in Table 8, aggregates were produced at the highest level in Control 1, which did not contain any stabilizer, and at the second highest level in Control 2, which was prepared using histidine as a stabilizer. In contrast, the liquid formulations of the present invention, with the exception of DWF16, never produced aggregates. These results indicate that a stable liquid formulation of human growth hormone may be prepared by combining a specific amino acid, L-lysine or L-arginine, or PEG 300, which serves as a stabilizer, with a specific surfactant.

In addition, the liquid formulations were examined for the residual rates of somatropin when stored at 25° C. for three months and at 2° C. to 8° C. for up to one year. The results are given in Table 9, below, and FIGS. 1 and 2.

TABLE 9

| | 25° C. (3 months) | | 2° C. to 8° C. (1 year) | |
|---|---|---|---|---|
| | Deamidation (somatropin %) | Aggregation (somatropin %) | Deamidation (somatropin %) | Aggregation (somatropin %) |
| DWF15 | 92.34 ± 0.20 | 98.24 ± 0.08 | 94.56 ± 0.12 | 99.78 ± 0.02 |
| DWF16 | 93.15 ± 0.15 | 98.45 ± 0.06 | 95.64 ± 0.05 | 99.43 ± 0.03 |
| DWF17 | 95.26 ± 0.19 | 100.00 ± 0.00 | 98.06 ± 0.05 | 100.00 ± 0.00 |
| DWF18 | 94.56 ± 0.18 | 99.93 ± 0.03 | 99.17 ± 0.09 | 100.00 ± 0.00 |

Figure 2:
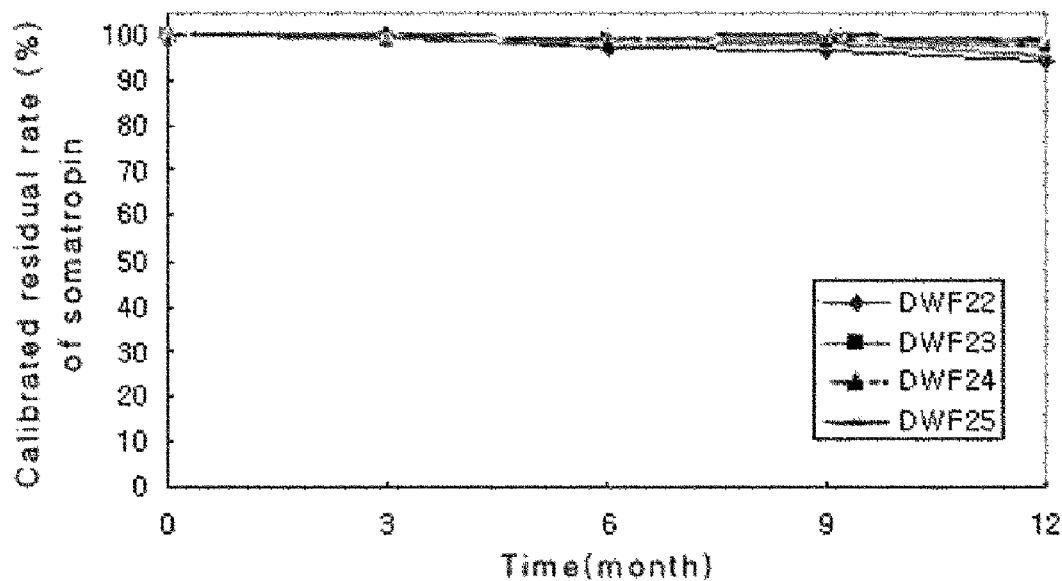
FIG. 2 is a graph showing the residual rate (%) of human growth hormone according to deamidation and aggregation when a liquid formulation according to the present invention is stored at 2° C. to 8° C. for one year.
Figure 2:
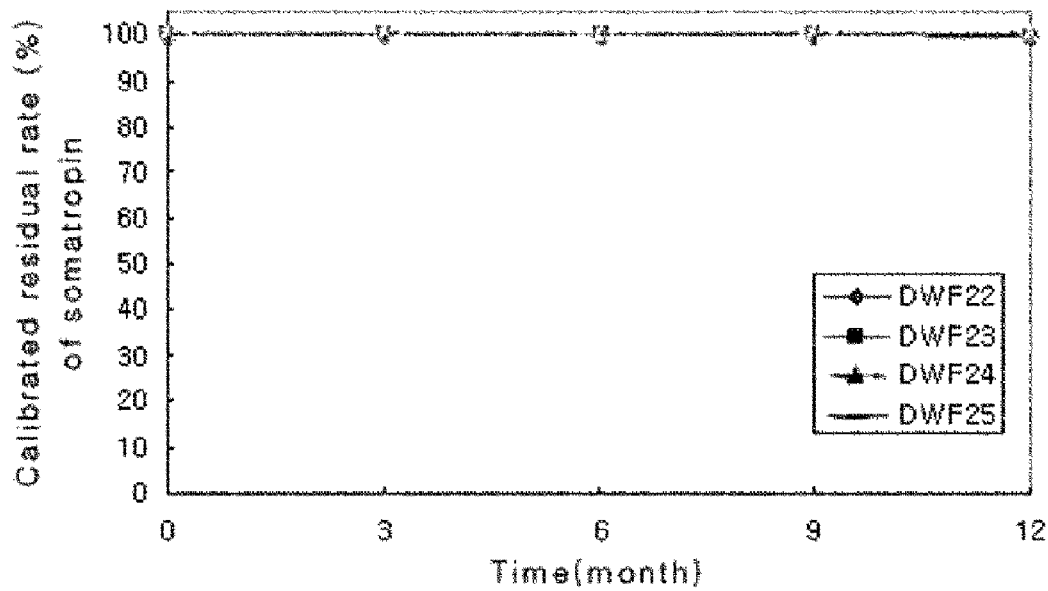

As shown in Table 9 and FIGS. 1 and 2, the liquid formulations were stable during storage for a period of at least one year.

Industrial Applicability

As described hereinbefore, the present invention employed a specific stabilizer in combination with a specific surfactant in order to overcome the problem of low stability of a liquid formulation of human growth hormone, thereby suppressing the formation of deamidated products of human growth hormone and, in particular, preventing aggregation into dimers or polymers, leading to remarkably enhanced stability. Thus, the liquid formulation according to the present invention is highly resistant to external stresses during transport and storage.

The invention claimed is:

1. A liquid formulation comprising human growth hormone; L-lysine or L-arginine; and poly(oxyethylene) poly(oxypropylene) copolymer 188, polyethylene glycol-15 polyoxystearate or polyethylene glycol-35 castor oil,
    wherein the human growth hormone is present in an amount ranging from 2.5 to 5.5 mg/ml; the L-lysine or L-arginine in an amount ranging from 0.02 to 0.5% (w/v) per mg of the human growth hormone; and the poly(oxyethylene) poly(oxypropylene) copolymer 188, polyethylene glycol-15 polyoxystearate or polyethylene glycol-35 castor oil in an amount ranging from 0.1 to 0.5% (w/v).

2. The liquid formulation according to claim 1, wherein the L-lysine or L-arginine is a hydrochloride salt.

3. The liquid formulation according to claim 1, further comprising at least one selected from among a buffer, an isotonic agent, a preservative and an analgesic.

4. The liquid formulation according to claim 3, wherein the human growth hormone is present in an amount ranging from 2.5 to 5.5 mg/ml; the L-lysine or L-arginine in an amount ranging from 0.02 to 0.5% (w/v) per mg of the human growth hormone; the poly(oxyethylene) poly(oxypropylene) copolymer 188, polyethylene glycol-15 polyoxystearate or polyethylene glycol-35 castor oil in an amount ranging from 0.1 to 0.5% (w/v); sodium citrate or sodium acetate in an amount ranging from 5 to 20 mM; D-mannitol in an amount ranging from 20 to 50 mg/ml; and benzyl alcohol in an amount ranging from 1 to 9 mg/ml.

* * * * *